United States Patent [19]
Toth

[11] Patent Number: 5,476,105
[45] Date of Patent: Dec. 19, 1995

[54] ABDUCTION PILLOW FOR ORTHOPEDIC SUPPORT

[76] Inventor: Julie O. Toth, 6601 Rosedale 988-7912, Amherst, Ohio 44001

[21] Appl. No.: 201,451

[22] Filed: Feb. 24, 1994

Related U.S. Application Data

[63] Continuation of Ser. No. 912,270, Jul. 13, 1992, Pat. No. 5,289,828.

[51] Int. Cl.⁶ .................................................. A61G 15/00
[52] U.S. Cl. ................................ 128/845; 128/DIG. 20
[58] Field of Search ........................... 128/845, DIG. 20; 602/13, 23, 24; 5/624, 648, 644, 651

[56] References Cited

U.S. PATENT DOCUMENTS

| | | | |
|---|---|---|---|
| 2,709,435 | 5/1955 | Krass | 128/260 |
| 3,532,336 | 10/1970 | Baker | 269/328 |
| 3,742,528 | 7/1973 | Munch | 5/91 |
| 3,843,980 | 10/1974 | Rodriguez | 5/327 R |
| 3,901,228 | 8/1975 | Brown | 128/133 |
| 3,931,654 | 1/1976 | Spann | 5/327 |
| 4,071,031 | 1/1978 | Lowman | 602/13 |
| 4,090,268 | 5/1978 | Turner | 5/648 |
| 4,135,504 | 1/1979 | Spann | 128/80 A |
| 4,169,467 | 10/1979 | Rabischong | 602/13 |
| 4,265,232 | 5/1981 | Stonich | 128/133 |
| 4,392,489 | 7/1983 | Wagner, Sr. | 128/80 A |
| 4,520,805 | 6/1985 | Vincent et al. | 128/80 R |
| 4,566,449 | 1/1986 | Smith | 128/133 |
| 4,584,730 | 4/1986 | Rajan | 5/431 |
| 4,723,329 | 2/1988 | Vaccaro | 5/449 |
| 4,754,510 | 7/1988 | King | 5/431 |
| 4,779,296 | 10/1988 | Bond | 5/436 |
| 4,805,605 | 2/1989 | Glassman | 128/80 A |
| 4,889,109 | 12/1989 | Gifford | 128/80 A |
| 4,910,818 | 3/1990 | Grabill et al. | 5/443 |
| 4,944,059 | 7/1990 | Wall | 5/449 |
| 5,033,137 | 7/1991 | Pedrow | 5/436 |
| 5,113,875 | 5/1992 | Bennett | 128/845 |
| 5,134,739 | 8/1992 | Gaffe | 5/648 |
| 5,289,828 | 3/1994 | Toth | 5/648 |

Primary Examiner—Michael A. Brown
Attorney, Agent, or Firm—Sand & Sebolt

[57] ABSTRACT

An abduction pillow used to immobilize a patient's legs after hip surgery has a wedge-shaped body constructed of a resilient deformable material which positions the legs in a forgiving, fixed divergent position. The body is wedge-shaped and preferably air filled, and has a pair of opposing sides which taper outwardly in a divergent manner from a narrow anterior end adapted to be located adjacent the groin area of a patient, toward a wider distal end. The body has an upper surface which inclines downwardly from the distal end toward the anterior end. A longitudinal arcuate recess is formed in the upper inclined surface and has a depth sufficient to support one of the patient's legs. The vertical distance between a plane in which the other of the patient's legs lies and the bottom of the longitudinal arcuate recess, is equal to the width of the wedge-shaped body at any transverse plane taken through the pillow. This dimensional relationship insures that the patient's legs and hips remain immobilized and at a constant spaced relationship even after the patient is turned onto either side.

14 Claims, 2 Drawing Sheets

ABDUCTION PILLOW FOR ORTHOPEDIC SUPPORT

CROSS REFERENCE TO RELATED APPLICATION

The present application is a continuation of patent application Ser. No. 07/912,270, filed Jul. 13, 1992, now U.S. Pat. No. 5,289,828.

BACKGROUND OF THE INVENTION

1. Technical Field

This invention relates generally to an orthopedic support. More particularly, the invention relates to abduction pillows. Specifically, the invention relates to abduction pillows used to immobilize legs after arthroplasty or endoprosthetic hemiarthroplasty surgery to accelerate the recovery and healing process.

2. Background Information

Post-operative management of patients having undergone total hip arthroplasty or endoprosthetic hemiarthroplasty usually includes measures to prevent early dislocation of the hip. Adduction generally increases the risk of dislocation of the hip and as such, pillows are used to immobilize the legs after surgery to facilitate and accelerate the healing process. Despite variations in base material, usually some form of foam rubber and associated covering, most pillows have basically the same design and makeup. This design includes a triangular shape such that the apex fits between the thighs near the patient's groin, and the broader base fits between the ankles, thereby maintaining the desired abduction. Retention straps attached to the pillow are then used to secure it in place by encircling the legs above and below each knee.

While the known abduction pillows are presumably sufficient for the purpose for which they are intended, several problems have been associated with their use. Specifically, decubitus ulcers, or bedsores, can result from the extended recumbent position of the patient thereby causing permanent stretch injuries to soft tissue. More particularly, the design of the current abduction pillows utilizes retention straps above and below the knees as set forth hereinabove. Because the pillow itself is generally fairly rigid, it acts as a splint to maintain the knee in full extension. With the legs cinched against the pillow, a situation can arise in which the buttocks proximally and the heel distally are the only firm points of contact between the leg and the bed. The heel then supports a large portion of the weight of the leg, distributing it over a very small surface area.

This condition is aggravated by the fact that in the immediate post-operative state, the patient is usually heavily sedated, and often is given high doses of narcotic analgesics. As a result, the normal protective sensations, the body telling you when damage will occur, can be markedly impaired by theses medications. The situation is even more dramatic for a patient in whom spinal anaesthesia has been used, as that they may have no protective sensation in the lower extremities of their body for hours. To overcome the above problems the patient is turned many times through the day to assure that no particular point of the patient's body is subject to localized pressures for an extended period of time. However, the constant turning requires a significant number of pillows and supports to assure that the patient, when turned, remains turned.

A second problem generally associated with the prior art abduction pillows relates to the use of straps to cinch the leg against the pillow. In operation, the straps must be sufficiently tight to assure that the leg will not move with respect to the abduction pillow positioned between the patient's leg. However, if the straps are set too tight, neurovascular complications can result within the leg. Such complications can be avoided by designing an abduction pillow wherein the use of straps to cinch the leg against the abduction pillow is unnecessary.

Moreover, current abduction pillows are bulky and difficult to store. Also, a few days after a total hip arthroplasty surgery, the patient is removed from the bed several times a day in an attempt to get the patient onto his feet and moving about once again. The current abduction pillow makes this difficult, as the pillow must be completely removed from the patient, taken from in between the patient's legs, and stored while the patient attempts to walk.

Lastly, current abduction pillows inevitably result in difficulties with elimination and perennial care. These arise from the fact that conventional abduction pillows fit quite high between the thighs, such that in order to use a bedpan or a urinal, it is necessary to remove the retention straps and either completely remove the pillow or to slide it distally a significant distance. The same holds true for the performance of routine perennial care.

SUMMARY OF THE INVENTION

Objectives of the invention include providing an improved orthopedic device for supporting and positioning the lower extremities of a patient that has had hip arthroplasty.

Another objective is to provide an orthopedic device which will support and position the patients legs in two separate positions to aid in the healing process, and prevent decubiti from forming on the patient's bony prominences.

Yet another objective is to provide an orthopedic device which will support and elevate the patients heel to prevent decubitus ulcers from forming on the patients heels due to the patient rubbing his or her heel on the mattress causing friction.

Another objective is to provide an orthopedic device which allows the care giver to provide the necessary elimination and perennial care to the patient without completely removing the abduction pillow.

A further objective is to provide an abduction pillow which will be easily removed when the patient is out of bed, and requires little or no storage when not in use.

A still further objective is to provide an air inflatable abduction pillow which provides the necessary rigidity to support the patient's legs, while simultaneously providing the necessary forgiveness to assure that decubitus ulcers do not form on any portion of the patients legs.

Yet a further objective of the present invention is to provide an air inflatable abduction pillow which provides two support positions allowing the patient to be turned, with each position keeping the patient's legs in the correct abduction position, without employing cinching straps about the patient's legs.

A still further objective is to provide such an orthopedic support which is of a simple construction, which achieves the stated objectives in a simple, effective, and inexpensive manner, and which solves problems and satisfies needs existing in the art.

These and other objectives and advantages of the invention are obtained by the abduction pillow of the present invention used for supporting the legs of an orthopedic patient in first and second positions, such that the patient's legs remain in full extension in each of said two positions, said pillow comprising: a wedge-shaped body having sides tapered outwardly in a divergent manner from a first end adapted to be located adjacent a groin area of the patient, toward a wider second end, and an upper surface inclined downwardly from the second end toward the first end; and a longitudinally extending recess formed in the upper inclined surface extending from generally adjacent the first end to generally adjacent the second end; said recess having a bottom surface lying in a generally continuous plane and having a depth sufficient to support one of the patient's legs therein, with the vertical distance measured along a first plane between the bottom surface of the recess and a second plane which extends through the wedge-shaped body between the first and second ends, with said first plane being perpendicular to said second plane, being generally equal to the width of the wedge-shaped body when measured along the intersection of said first and second planes whereby the distance between the patient's legs in the first position wherein each of the patient's legs lies generally in the second plane adjacent a respective side of said wedge-shaped body, equals the distance between the patient's legs in the second position where one of the patient's legs lies generally in the second plane adjacent said side and the other of the patient's legs lies generally in said first plane supported in the recess.

BRIEF DESCRIPTION OF THE DRAWINGS

The preferred embodiment of the invention illustrative of the best mode in which applicant has contemplated applying the principles, is set forth in the following description and is shown in the drawings and is particularly and distinctly pointed out and set forth in the appended claims.

Similar numerals refer to similar parts throughout the drawings.

DESCRIPTION OF THE PREFERRED EMBODIMENT

Figure 1:
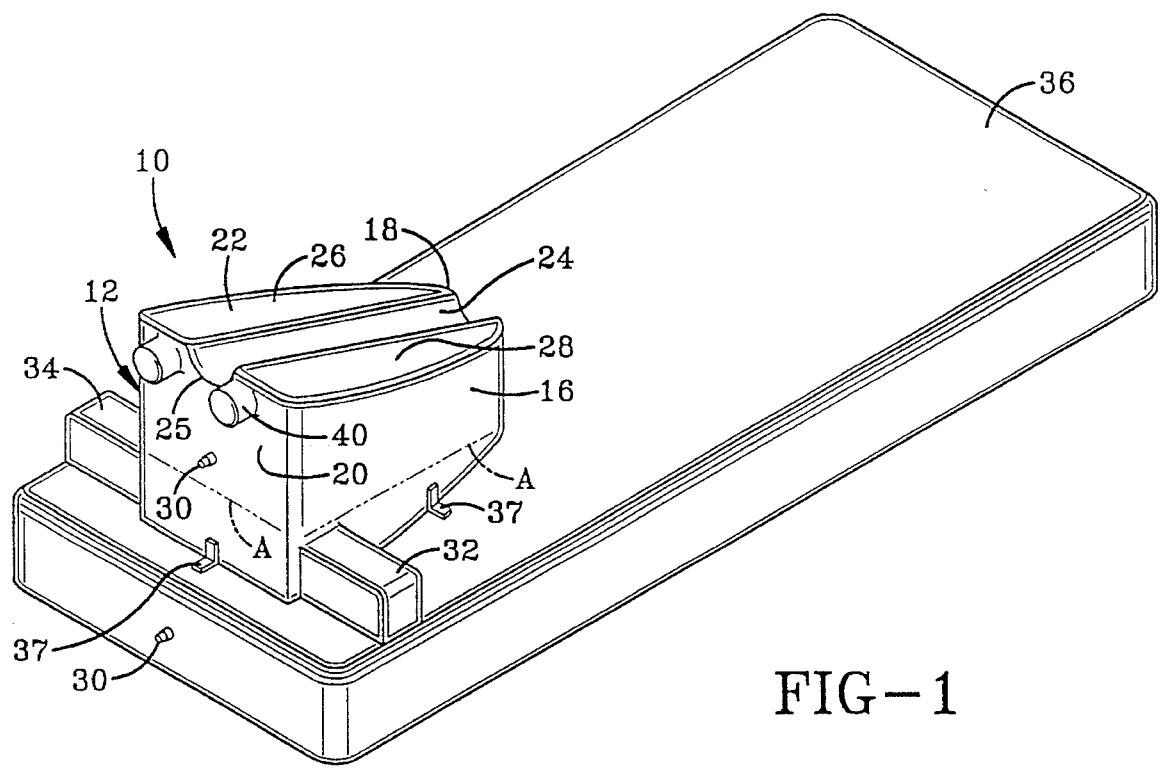
FIG. 1 is a perspective view of the improved abduction pillow supported on a mattress.

With reference initially to FIG. 1, it will be seen that an abduction pillow 10 in accordance with the present invention, includes a generally wedge-shaped body portion indicated generally at 12, having a pair of divergent sides 14 and 16. Sides 14 and 16 terminate at a first or anterior end 18 and an opposing wider distal end 20. In the preferred embodiment, anterior or first end 18 is within the range of from 4 inches to 8 inches, with 6 inches being the preferred width such that it may be placed easily between the upper thighs of a patient 17 as shown particularly in FIG. 3. Distal or second end 20 is significantly wider than anterior end 18 and in the preferred embodiment, is within the range of from 12 inches to 16 inches with 14 inches being the preferred width.

As such, sides 14 and 16 are divergent from anterior end 18 to distal end 20. Body 12 has a bottom surface 19 and an upper surface 22, which are hermetically sealed to the edges of sides 14 and 16 as well as ends 18 and 20, and are substantially planar in configuration.

In accordance with one of the main features of the invention, top surface 22 is formed with an arcuate recess 24 having a curved bottom surface 25 which extends along the longitudinal axis of surface 22 and provides a pair of spaced flat support surfaces 26 and 28 extending longitudinally on either side of the recess. There exists an imaginary horizontal plane depicted at A (FIG. 1), which bisects body 12 with the end of the plane near distal end 20 including the top surfaces of two protruding heel supports 32 and 34. Plane "A" intersects anterior end 18 at bottom surface 19. In essence, imaginary plane "A" lies at the approximate angle of elevation of the patient's legs.

In accordance with the present invention, the distance for imaginary plane "A" to surface 25 of arcuate recess 24 is equal to the width of body portion 12 in any given vertical plane taken transverse to the longitudinal axis of pillow 10. This relation will provide separate equal positions of abduction, and as such provide two positions for a patient to be placed without sacrificing the consistency of the relative position of the patient's legs. Moreover, this relationship will aid in supporting the patient's entire leg. Upper surface 22 is inclined upwardly from anterior end 18 toward distal end 20 to create the similarity between the distance from surface 25 to plane "A" and the width of the body portion 12 in any given vertical plane taken transverse to the longitudinal axis of the pillow 10. Similarly, the incline is necessary to assure that the patient's entire leg is supported.

By way of example, at distal end 20, the distance from surface 25 of arcuate recess 24 to plane "A" is equal to the width of distal end 20, which in the preferred embodiment is approximately 14 inches. Similarly, at anterior end 18, the distance between surface 25 and plane "A" is equal to the width of anterior end 18, which in the preferred embodiment is approximately 6 inches. Thus, the incline of upper surface 22 rises from 6 inches at anterior end 18 to 14 inches at distal end 20. It should be apparent to one skilled in the art that these heights and widths may be altered without departing from the spirit of the invention so long as the height of surface 25 with respect to the imaginary plane "A" remains similar to the width of body 12 in all vertical planes transverse to the longitudinal axis of pillow 10.

The height of support surfaces 26 and 28 above bottom surface 25 of recess 24 can be altered without departing from the spirit of the present invention. However, such height is preferably 2 inches. The height of such support surfaces 26 and 28 may be lessened as long as they will adequately support the lateral weight of the patient's leg. Moreover, the height could be increased so long as the abduction of the leg is not compromised by raising the leg over surfaces 26 and 28 to place the leg in arcuate recess 24.

Figure 2:
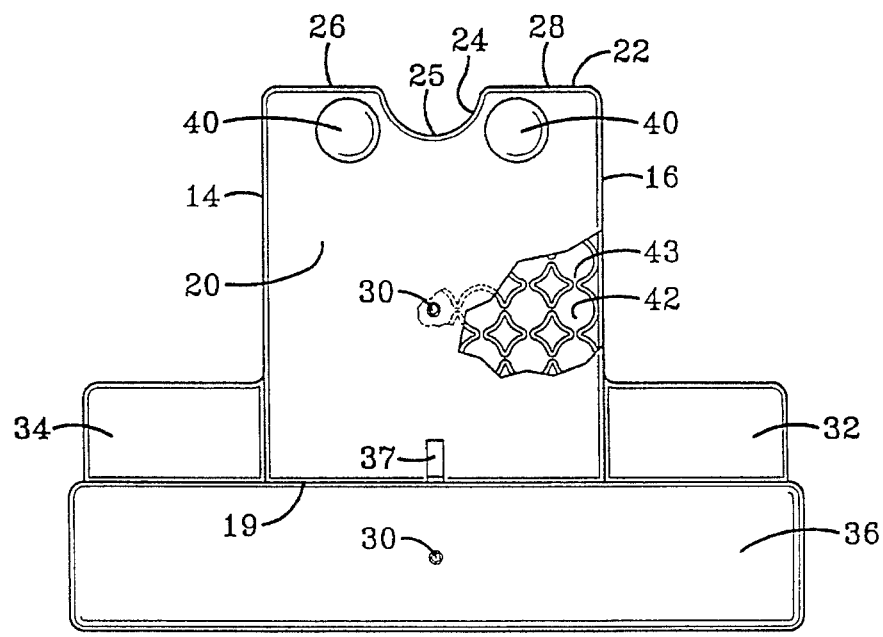
FIG. 2 is an end elevational view with portions broken away and in section, of the abduction pillow and mattress shown in FIG. 1.

Abduction pillow 10 may be created as a single hollow air inflatable unit formed of an air impervious material and inflated through a usual inflation valve 30 or inlet/outlet fluid port located in a convenient location on body 10. It also may be created from a plurality of independent air inflatable units, each having a separate inflation valve. In the preferred embodiment, body 12 is created from a plurality of interconnected tubes 42 as shown in FIG. 2, thereby providing the necessary rigidity to support the orthopedic patient's legs while simultaneously providing the necessary forgiveness to provide a more uniform weight distribution of the weight over the pillow's surface. Preferably the hollow interiors of the tube communicate with each other through passages 43 so that the tubes inflate and deflate simultaneously. If desired, pillow 10 may be liquid filled or formed of a resilient foam material, although an air inflatable unit is believed to best achieve the objective of the invention.

Extending from the lower portions of divergent sides 14 and 16 near the distal end 20, are a pair of heel supports 32 and 34, respectively. Heel supports 32 and 34 extend outwardly in a direction transverse to the longitudinal axis of body 12 and are of a sufficient height to elevate the patient's heel off of a support mattress 36 as shown particularly in FIG. 3. Heel supports 32 and 34 preferably have hollow interiors which communicate with the hollow interior of body 12 so that it will inflate and deflate with body 12.

Figure 4:
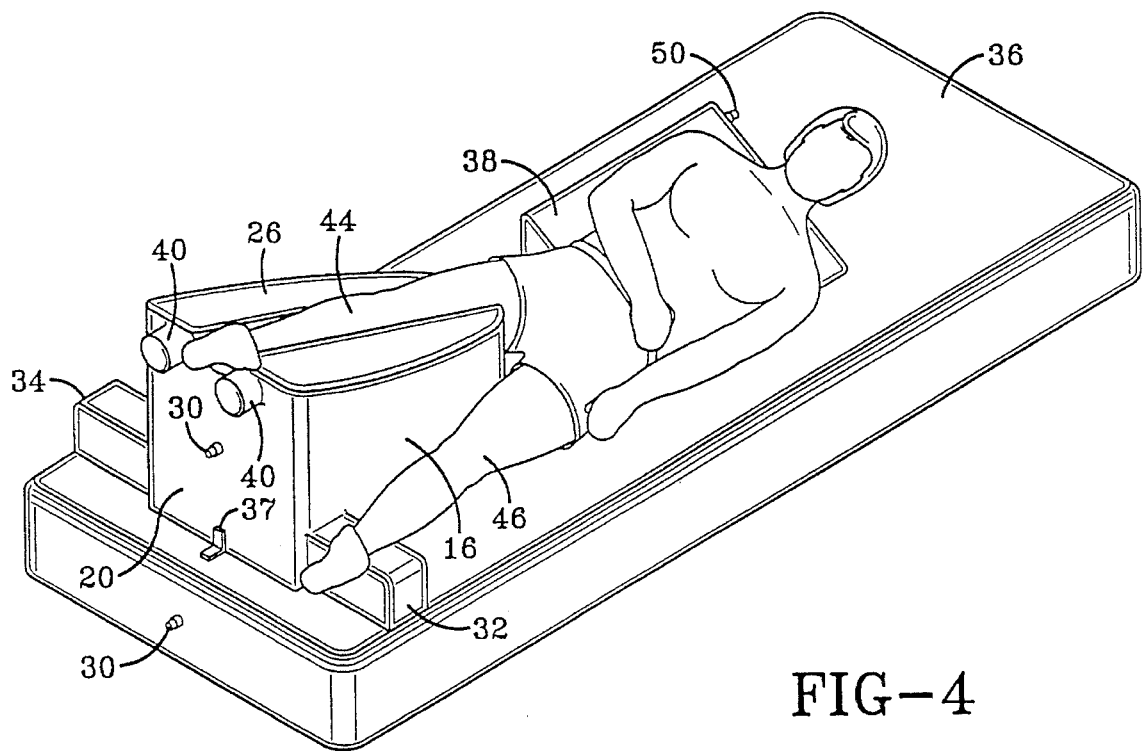
FIG. 4 is a perspective view similar to FIG. 3 showing the patient after having been turned on his/her side.

A pair of foot supports 40 preferably are formed integrally with body 12 and extend outwardly from distal end 20 closely adjacent arcuate recess 24 for selectively supporting the feet of patient 17, when the patient is lying in an orthopedic position as shown in FIG. 4.

When in use, pillow 10 will be supported on mattress 36 adjacent an end thereof. Mattress 36 may be of any conventional construction to which the abduction pillow may be attached by straps, Velcro strips 37, or any convenient attachment means. Mattress 36 may be a conventional foam-filled, spring-filled, or air-filled mattress. However, mattress 36 may also be integrally connected to abduction pillow 10 such that the mattress 36 and pillow 10 are a single unit. In such a situation, mattress 36 would be hermetically sealed apart from abduction pillow 10, such that the pillow could be inflated and deflated without affecting the inflation of mattress 36.

Figure 3:
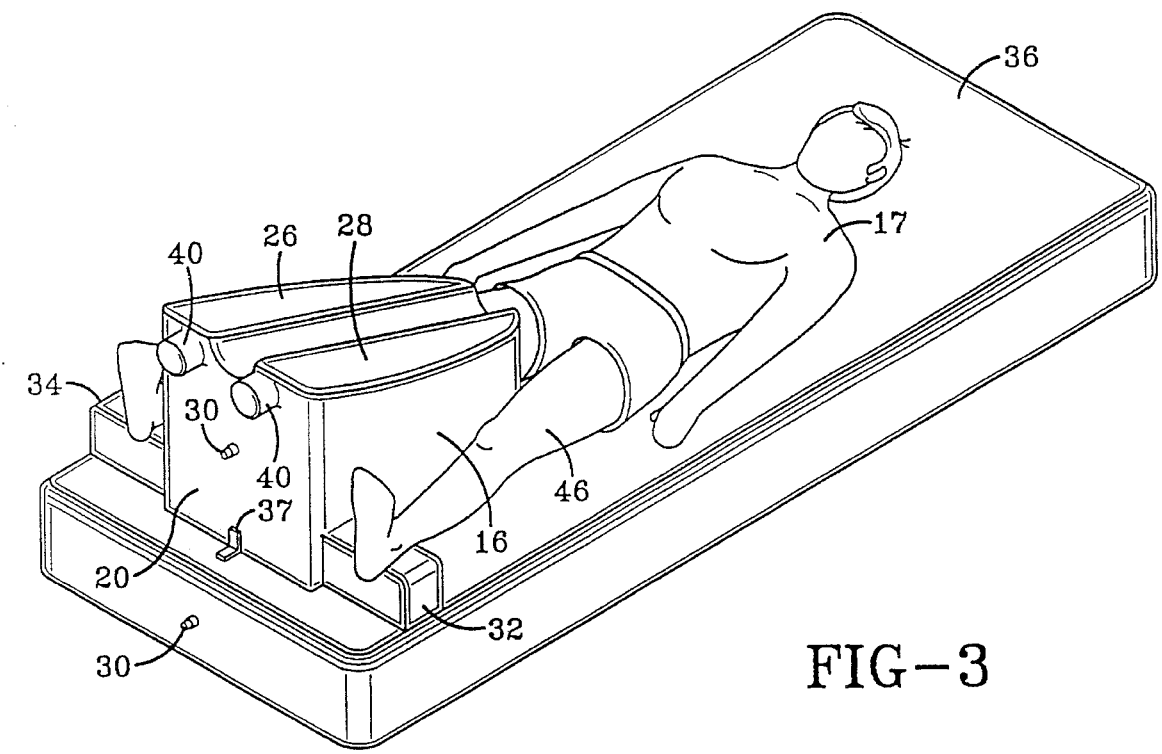
FIG. 3 is a perspective view of a patient laying on the mattress and using the abduction pillow as shown in FIG. 1.

Having now described the orthopedic support of the present invention in detail, the use of the support for immobilizing the legs of orthopedic patients is set forth below. Referring then to FIG. 3, there is shown a patient 17 recumbent on mattress 36 in the first position of abduction with pillow 10 being employed to prevent damage to the hip after having total hip arthroplasty and endoprosthetic hemi-arthroplasty. In an effort to prevent early dislocation, the patient is recumbent on mattress 36 with body 12 of pillow 10 interposed between the patient's legs such that legs 44 and 46 are positioned proximal to sides 14 and 16, respectively. The patient's ankles are then supported by heel supports 32 and 34 to elevate the patient's heels off of mattress 36 thereby preventing decubitus ulcers from forming on the heels of the patients. In this position, the patient's legs remain a consistent distance apart as dictated by the width of abduction pillow 10.

Just as decubitus ulcers can form on a patient's heels when recumbent for an extended period of time, such ulcers can form at many other bony prominences on the patient's body which carry the majority of the patient's weight and distribute it upon a comparatively small cross-sectional area. While the use of mattress 36 aids in weight distribution in that the mattress forms more closely to the patient's body, the patient still must be frequently turned to prevent such ulcers from forming. As such, a second position for abduction is necessary, and is shown in FIG. 4. Specifically, the patient is turned forty-five degrees with his leg being lifted over either surface 26 or 28 depending upon the direction the patient is turned, and placed into arcuate recess 24. Inasmuch as the distance between the bottom surface 25 of arcuate recess 24 and plane A of body 12 is equal to the width of the abduction pillow in any plane transverse to the longitudinal axis of the pillow 10, the distance between the legs 44 and 46, and consequently the percent of abduction, remains constant. In this manner, the present invention provides two independent positions of abduction with each position presenting the exact same abduction as the other which allows the patient to be turned without upsetting the abduction of the legs 44 and 46.

As is evident in FIG. 4, the patient in the second position of abduction is lying at an angle of approximately forty-five degrees. As such, the patient's back and neck must be supported in the same plane as that of the elevated leg to assure that the hip does not rotate. In the prior art, the patient is supported with a series of pillows that must be repeatedly checked and secured by the care givers. In order to prevent the need for care givers to constantly check the back and neck support of the orthopedic patient, the present invention also provides a wedge-shaped pillow 38, to be fitted under the patient's back to support the patient in the inclined position. Pillow 38 may be integrally formed with air mattress 36 such that when separately inflated through a inflation valve 50, it will actually move the patient as it is inflated. Thus, such a mattress would be provided with a pair of inflatable pillows 38 to be selectively used, depending upon whether the right or the left leg is to be moved. As shown in FIG. 4, a left wedge-shaped pillow 38 is in the inflated position supporting the user. Alternatively, pillow 38 may be a separate unit unattached to mattress 36 such that the pillow 38 can be moved from side to side as is necessary. It should also be apparent that the wedge-shaped pillow could be formed of any standard material such as foam, padding etc. without departing from the spirit of the present invention.

As described above, the patient's back and neck must be supported when in the second orthopedic support position of FIG. 4. In this position, the patient's foot extending from arcuate recess 24 must also be supported. The adjacent foot support 40 thus prevents the weight of the foot from causing the foot to hang downward.

It is thus seen that an abduction pillow has been provided which permits the patient to be turned in the bed or positioned on his side while the limbs are supported and fixed against rotation. The continuous support is provided for the full length of the leg and the support may be readily personalized by increasing or decreasing the air inflation to suit individual patients. The leg is supported at all times in a manner to prevent foot drop and to prevent cutting off of circulation as might result in the formation of decubitus ulcers. The attention time of nurses and other hospital personnel to the patient is reduced since the patient may be left unattended for greater periods of time due to the secure support provided by pillow 10.

Accordingly, the orthopedic support of the present invention is simplified, provides an effective, safe, inexpensive, and efficient device which achieves all the enumerated objectives, provides for eliminating difficulties encountered with prior devices, and solves problems and obtains new results in the art.

In the foregoing description, certain terms have been used for brevity, clearness and understanding; but no unnecessary limitations are to be implied therefrom beyond the requirement of the prior art, because such terms are used for descriptive purposes and are intended to be broadly construed.

Moreover, the description and illustration of the invention is by way of example, and the scope of the invention is not limited to the exact details shown or described.

Having now described the features, discoveries and prin- ciples of the invention, the manner in which the improved orthopedic support is constructed and used, the characteristics of the construction, and the advantageous, new and useful results obtained, the new and useful structures, devices, elements, arrangements, parts and combinations, are set forth in the appended claims.

I claim:

1. An abduction pillow for supporting the legs of an orthopedic patient in first and second positions, such that the patient's legs remain in full extension in each of said two positions, said pillow comprising: a wedge-shaped body having sides tapered outwardly in a divergent manner from a first end adapted to be located adjacent a groin area of the patient, toward a wider second end, and an upper surface inclined downwardly from the second end toward the first end; a longitudinally extending recess formed in the upper inclined surface extending from generally adjacent the first end to generally adjacent the second end; said recess having a bottom surface lying in a generally continuous plane and having a depth sufficient to support one of the patient's legs therein; a first plane extending between the bottom surface of the recess and a second plane; the second plane extending perpendicular to the first plane, through the wedge shaped body and between the first and second ends; and a vertical distance measured in the first plane between the bottom surface of the recess and the second plane which is generally equal to the width of the wedge-shaped body when said width is measured at the intersection of said first and second planes whereby the distance between the patient's legs in the first position wherein each of the patient's legs lies generally in the second plane adjacent a respective side of said wedge-shaped body, equals the distance between the patient's legs in the second position where one of the patient's legs lies generally in the second plane adjacent said side and the other of the patient's legs lies generally in said first plane supported in the recess.

2. An abduction pillow as described in claim 1 in which the wedge-shaped body is formed of a fluid impervious material; and in which at least one inlet/outlet fluid port is provided on the body for inflating and deflating said abduction pillow.

3. An abduction pillow as described in claim 1 in which the body has a pair of opposed sides extending between the first and second ends; and in which a heel support extends outwardly from each of said opposed sides having a height sufficient to elevate the patient's heels.

4. An abduction pillow as described in claim 3 in which the heel supports are formed integrally with the wedge-shaped body and are constructed of a fluid impervious material.

5. An abduction pillow as described in claim 3 in which the wedge-shaped body has a hollow interior which communicates with a hollow interior of the heel supports such that the inflation or deflation of the pillow results in inflation and deflation of the heel support.

6. An abduction pillow as described in claim 1 including attachment means for attaching said abduction pillow to a supporting mattress.

7. An abduction pillow as described in claim 2 in which the wedge-shaped body is formed integrally with a lower supporting mattress.

8. An abduction pillow as described in claim 7 wherein said mattress is provided with a fluid inlet/outlet port whereby said mattress may be inflated and deflated separately from the wedge-shaped body.

9. An abduction pillow as described in claim 1 in which a pair of foot supports extend outwardly from the second end of the body adjacent the longitudinal recess for alternately supporting the patient's feet when the patient's legs are selectively supported in said recess.

10. An abduction pillow as described in claim 1 in which the wedge-shaped body includes a plurality of deflatable fluid-impervious, fluid-filled tubes.

11. An abduction pillow as described in claim 10 in which hollow interiors of the fluid filled tubes communicate with each other such that the tubes inflate and deflate simultaneously.

12. An abduction pillow as described in claim 10 in which the tubes are air filled; and in which an inflation valve communicates with at least one of said tubes.

13. An abduction pillow as described in claim 1 in which said longitudinal recess is arcuate.

14. An abduction pillow as described in claim 1 in which the width of the second end is in the range of from 12 inches to 16 inches; and in which the width of the first end is in the range of from 4 inches to 8 inches.

* * * * *